United States Patent [19]

Samaria

[11] Patent Number: 4,666,451
[45] Date of Patent: May 19, 1987

[54] CLAMP TO BE ACTUATED BY A HAND PROTHESIS

[76] Inventor: Carlos E. E. Samaria, Montevideo 865, Buenos Aires, Argentina

[21] Appl. No.: 874,430

[22] Filed: Jun. 16, 1986

[51] Int. Cl.⁴ ............................................. A61F 2/68
[52] U.S. Cl. .................................... 623/65; D7/105; 294/25
[58] Field of Search .......................... D7 105; D8 57; 128 22; 128 23; 128 24; 128 354; 128 346; 128 356; D24 26; D24 27; 623/65; 294/25, 99.2 294/902; 30/298, 253–262; 401/7, 8

[56] References Cited

U.S. PATENT DOCUMENTS

| D. 101,791 | 11/1936 | Rach | D8/57 |
| D. 148,919 | 3/1948 | Duncan | D7/105 |
| D. 189,488 | 12/1960 | Page | D7/105 |
| D. 239,910 | 5/1976 | Megna | D8/57 |
| 277,531 | 5/1883 | Aclserman | 294/99.2 |
| 2,184,909 | 12/1939 | Crompton | 30/256 |
| 3,648,701 | 3/1972 | Botts | 128/321 |
| 4,120,302 | 10/1978 | Ziegler | 128/346 |
| 4,261,608 | 4/1981 | Bradshaw | D7/105 |

Primary Examiner—Richard J. Apley
Assistant Examiner—James Prizant
Attorney, Agent, or Firm—Gilbert L. Wells

[57] ABSTRACT

The instant invention refers to a clamp to be used by persons whose hand has been amputated and use hand protheses actuating fingers by means of electrical or mechanical command mechanisms. Since in most cases these elements do not permit grasping or seizing a great variety of sizes and shapes of objects, this clamp constitutes an auxiliary element widening the range of possibilities of said hand protheses.

The clamp is a tool comprising two substantially equal arms, mutually articulated at an end, the opposite ends being equal and symmetrical, shaped to grasp objects, including at their intermediate regions solidary rings to introduce the thumb, the forefinger and the middle finger corresponding to the prothesis, the central opening of said rings having cylindrical configuration and rounded edges, there being one ring for one arm and two adjacent rings for the other having different orientation therebetween; the planes of the ring openings of the second arm and plane of the ring opening of the first arm defining corresponding dihedral angles smaller than 180°, each arm defining a third class lever, the resistance end of which is constituted by the free end of said arms.

5 Claims, 6 Drawing Figures

U.S. Patent    May 19, 1987    4,666,451
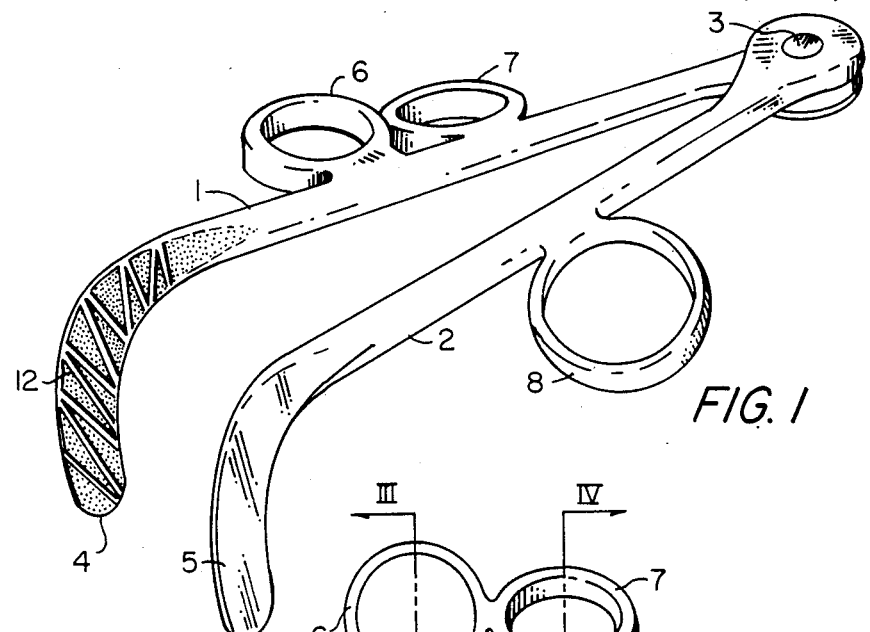
FIG. 1
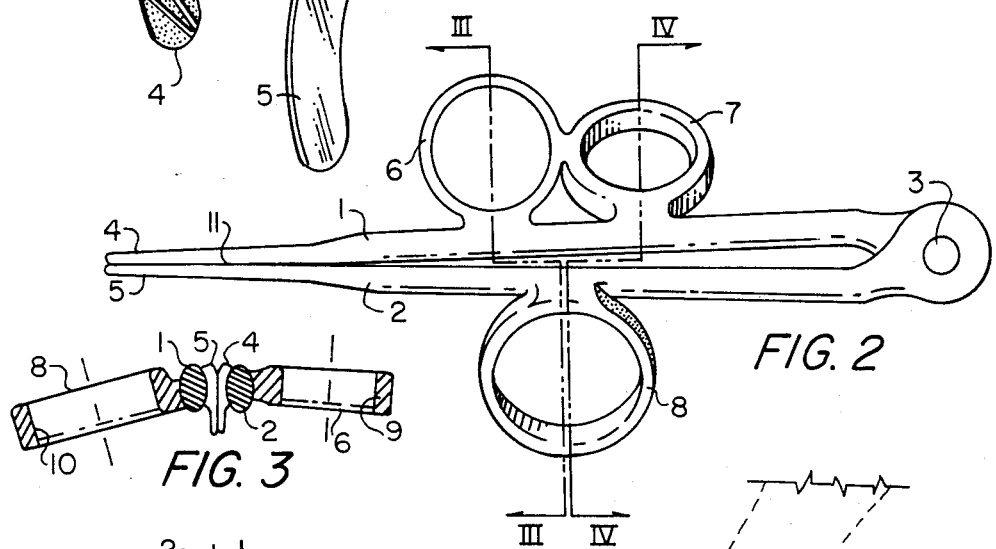
FIG. 2
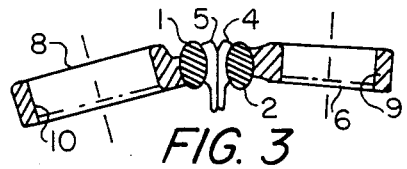
FIG. 3
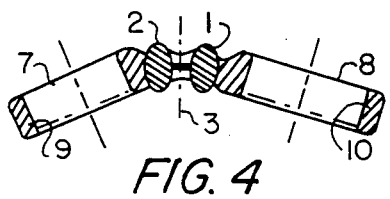
FIG. 4
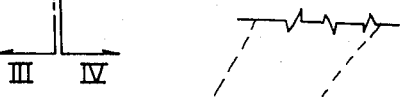
FIG. 5
FIG. 6
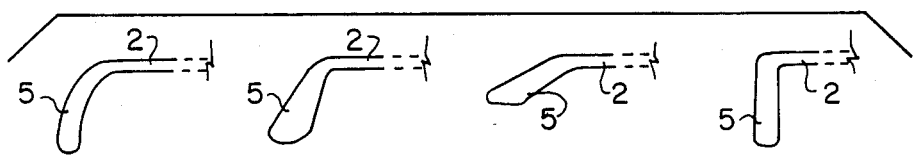

CLAMP TO BE ACTUATED BY A HAND PROTHESIS

FIELD OF THE INVENTION

The instant invention relates to a clamp to be actuated by a hand prothesis, which widens and improves the function of said prothesis.

More particularly, the instant invention relates to a clamp of the specified type specially developed for persons whose hand has been amputated and use hand protheses of the kind in which each prothesis has some of its fingers actuated by means of mechanical or electrical command mechanisms.

BACKGROUND OF THE INVENTION—PRIOR ART

It is known that, among the various resources used at present to give the persons whose hand has been amputated the possibility of developing in different works, although with limited efficiency, hand protheses with some movable fingers outstand, since these also provide a set of configuration, color and texture aspects, which imitate almost perfectly a natural human hand. The actuating means for said fingers, mechanical or electrical, provide movements of reduced amplitude and of generally limited forces.

The functioning conditions of said hand protheses reduce the range of aptitudes of the patient, even when using additional fingers permitting modification of their position, rotary wrists, etc. For this reason, orthopedy investigation is growing in order to find solutions for increasing the aptitude of said persons.

SUMMARY OF THE INVENTION

The clamp of the instant invention constitutes an accessory element or complement to be used by persons having hand protheses as those mentioned, without introducing any modification or adding any means to permit grasping or seizing a wider variety of sizes and shapes of objects, to grasp them even in the case a greater effort is required, to hold thlem more securely, etc.; the above represents an important improvement in the functional results provided by said protheses, as compared to the results obtained when hand protheses are used directly without the use of this new type of clamp.

In fact, the clamp of the invention comprises a tool formed by two substantially equal arms, mutually articulated at one end and having a shape permitting grasping objects at the other end, including special rings solidary to said arms, at the respective intermediate regions, so that in one arm a ring is fixed for introducing therein the thumb of the prothesis and in the other arm two rings are fixed, one for the forefinger and the other for the middle finger of the prothesis.

The configuration of the clamp permits taking advantage of the reduced movements of said hand prothesis. Conventionally, said protheses have a thumb capable of moving towards and outwards of the forefinger and middle finger; in turn these latter fingers may jointly move in a direction opposite to that of the thumb, i.e. jointly moving towards or outwards the thumb. The displacements of these three fingers are of reduced magnitude; but once they are inserted in the corresponding rings of the clamp of the invention, the ends of both arms, due to the articulated connection in the opposed end, approach and separate in a greater extent, giving consequently a wider shape and size range of the objects to be seized.

In the same way, the cited hand protheses have their forefinger and middle finger governed by a fork connecting rod, each of the branches of which corresponds to one of said fingers; therefore, the force driving the connecting rod is distributed in two components, one per finger; therefore, the intensity of each component is a half of the total force given by the mechanism, either electrical or mechanical. When an object is seized with one of those fingers and the thumb, the effective force is the force of only one of said components, therefore it is a generally reduced force. On the other hand, if the clamp of the invention is used, when the forefinger and the middle finger jointly actuate on one of its arms, the effective force will be obviously greater permitting grasping heavier objects or accomplishing greater efforts than those attained without the use of the clamp.

In order to properly fit the clamp of the invention in one of the cited hand protheses, the rings of both arms have slopes corresponding to the direction of the three mentioned fingers. Consequently, said slopes are mutually different, so that the upper openings of the rings are on corresponding different oblique planes. The planes corresponding to the openings of thumb and forefinger rings form a dihedral angle somewhat smaller than 180° in the faces opposed to the hand palm; while the planes corresponding to the middle finger and the thumb form a dihedral angle somewhat smaller than the first one.

On the other hand, since the outer surface of the synthetic material imitating texture and color of human skin of which said protheses are made is extremely sensitive and delicate, the rings of the clamp of the invention have a cylindrical-shaped inner surface, with rounded edges, in order not to provide sharp edges which may damage said material.

The articulation means between the arms of the clamp of the invention avoids distortion of said arms when they are operating, so that the slope angle of each ring and also the direction of the grasping ends are maintained. To this end, said articulation may have frictional contact planes perpendicular to the mutual connecting pin.

In what concerns to the mentioned grasping arms, the clamp of the invention may be made in accordance with several alternatives, without affecting in any way the intended scope of protection. Both arms are substantially rectilinear from the articulation up to a point passing the rings; in a first embodiment, these arms curve from a certain point passing the rings, covering parallel arcs of about 90° and have internal faces approximately planar, preferably with pierced grooves in order to give a somewhat rough surface to facilitate retention of the seized objects; another alternative provides the addition of a non-skidding material coating on opposite faces; another alternative provides the ends in the form of faced platelets, aligned or unaligned with the remaining portion of each arm, etc.

In order to explain the above advantages, to which the users and those skilled in the art may add many others, and to facilitate the understanding of the constructive, constitutive and functional characteristics of the clamp of the invention, a preferred embodiment will be described hereinbelow, which is schematically shown in the drawings without a determined scale. It is to be noted that since this embodiment constitutes an example, it is not intended to limit the scope of protection of the instant application.

BRIEF DESCRIPTION OF THE DRAWINGS

FIG. 1 is a perspective view of a clamp actuated by a hand prothesis in accordance with the invention.

FIG. 2 is a plan view of the same clamp.

FIG. 3 is a cross section of the clamp along line III—III of FIG. 2.

FIG. 4 is a cross section of the clamp along line IV—IV of FIG. 2.

FIG. 5 is a perspective view in which the same clamp is shown, in operating position in a hand prothesis in which the thumb, forefinger and middle finger are movable.

FIG. 6 comprises four schemes in which some of the multiple grasping configurations are shown, which may be adopted for the free ends of the clamp of the invention.

In all figures, the same reference numerals correspond to the same or equivalent parts or elements constituting the assembly and alternative embodiments selected as examples in this specification.

DETAILED DESCRIPTION OF THE INVENTION

As may be seen in the figures, particularly in FIGS. 1 and 2, the clamp of the invention comprises a tool formed by two rigid arms 1 and 2, mutually articulated in one of their ends by means of a pin 3, constituting corresponding third class levers, in which the fulcrum is common and coincides with said pin 3. The opposite ends of said arms, where the resistance is exerted, i.e. the free ends of said arms, are indicated with references 4 and 5; while the regions on which power is exerted are in intermediate positions, and wherein three rings are located, i.e. two of them, 6 and 7, on arm 1, and the third one is fixed to arm 2 and is indicated by reference 8. These rings are located approximately at half length of both arms and receive corresponding fingers of a hand prothesis with relatively tight fit.

In accordance with the above, said rings should comply with various requirements which may be seen in the figures. In the first place, their slopes are such that correspond to the directions conventionally used for the fingers of the hand prothesis, so that the forefinger tightly fits into ring 6 as shown in FIG. 5, the middle finger fits into ring 7 and the thumb into ring 8. Secondly, the configuration of said rings should comprise a substantially cylindrical surface in the interior of their central openings, as may be seen in FIG. 3, in which the internal surfaces 9 and 10 are cylindrical and have their opposite edges rounded in order not to damage the outer surfaces of the fingers of the prothesis.

The mentioned slopes of the rings may also be seen in FIGS. 3 and 4, in which the mentioned dihedral angles of less than 180° are illustrated.

In what concerns to the free ends of both arms, designated with references 4 and 5, their configuration comprises opposite faces, which may preferably contact on a plane 11 indicated in FIG. 2, in order to assure a maximum approach permitting grasping thin objects, even papers and the like. It is convenient that said faces have pierced grooves as those indicated with reference 12 in FIG. 1, or be coated with non-skidding materials, not shown, in order to aid in seizing the objects. Said ends 4 and 5 may have other shapes, in accordance with the specific requirements. FIG. 6 shows some alternatives within the scope of the invention. Besides, said ends may be spoon-shaped or have any shape common to known clamps such as those for grasping sugar lumps or ice, etc. without affecting the nature of the invention.

The axis of the articulation pin 3 should be parallel to the plane 11 shown in FIG. 2, thus assuring a correct facing of the inner surfaces of the free ends. In turn, it is convenient that the articulation has frictional contact planes perpendicular to said pin 3 to cooperate in the mentioned permanent facing of the free ends, always within the range of possible openings for the clamp actuated by the internal mechanism of the mentioned hand prothesis.

When carrying out the orthopedic clamp of the invention, modifications and or improvements may be included all of which should be considered as alternative embodiments within the scope of the instant invention, said scope being determined by the spirit of the appended claims.

I claim:

1. Clamp to be actuated by a hand prothesis, in which said prothesis is of the type imitating the human hand in what concerns to shape and preferably in what concerns to natural color and texture, including mechanical or electrical driving mechanisms for effecting approaching and separating movements between the thumb and the pair formed by the forefinger and the middle finger; said fingers being oriented in directions substantially opposed to the forearm of said prothesis, wherein said clamp is constituted by two rigid elongated arms, mutually articulated in one of their ends and having at their opposed ends corresponding configurations for grasping objects, which have opposite faces preferably planar, equal and symmetrical; while said arms, approximately at half of their lengths are solidary to rings the central opening of which has a cylindrical internal surface and rounded edges, there being one ring on one arm and two adjacent rings on the other; the first ring being oriented oppositely to the other two; said rings having corresponding slopes mating with the direction of the thumb, forefinger and middle finger of said prothesis; the plane of the openings of the rings on the second arm and of the opening of the ring of the first arm forming corresponding dihedral angles smaller than 180°, each arm defining a third class lever the fulcrum of which coincides with the end relative articulation pin, the power points being the rings and the resistance points being the free ends.

2. Clamp as claimed in claim 1, wherein the configurations of equal and symmetrical opposite ends comprise curved and flattened portions, their faces being provided with non-skidding grooves.

3. Clamp as claimed in claim 1 wherein the equal, symmetrical, curved and flattened free ends are coated with a non-skidding material.

4. Clamp as claimed in claim 1, wherein the equal and symmetrical free ends comprise facing concave surfaces.

5. Clamp as claimed in claim 1, wherein the equal and symmetrical free ends include corresponding sharp teeth.

* * * * *